US011771353B2

(12) United States Patent
Khasnobish et al.

(10) Patent No.: US 11,771,353 B2
(45) Date of Patent: Oct. 3, 2023

(54) STRESS LEVEL MONITORING OF USERS USING A RESPIRATORY SIGNAL AND ALERTING THEREOF

(71) Applicant: Tata Consultancy Services Limited, Mumbai (IN)

(72) Inventors: Anwesha Khasnobish, Kolkata (IN); Arijit Chowdhury, Kolkata (IN); Tanushree Banerjee, Kolkata (IN); Debatri Chatterjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 197 days.

(21) Appl. No.: 16/934,553

(22) Filed: Jul. 21, 2020

(65) Prior Publication Data

US 2021/0022656 A1 Jan. 28, 2021

(30) Foreign Application Priority Data

Jul. 22, 2019 (IN) .............................. 201921029445

(51) Int. Cl.
*A61B 5/00* (2006.01)
*A61B 5/16* (2006.01)
(Continued)

(52) U.S. Cl.
CPC ................ *A61B 5/165* (2013.01); *A61B 5/08* (2013.01); *A61B 5/7225* (2013.01);
(Continued)

(58) Field of Classification Search
None
See application file for complete search history.

(56) References Cited

U.S. PATENT DOCUMENTS

| 2005/0119586 A1* | 6/2005 | Coyle .................. A61B 5/1135 600/538 |
| 2014/0257122 A1* | 9/2014 | Ong .................... A61B 5/02405 705/2 |
| 2018/0184901 A1* | 7/2018 | Akmandor ........... A61B 5/0024 |

FOREIGN PATENT DOCUMENTS

| CN | 104274191 A * | 1/2015 |
| EP | 2281506 B1 | 1/2013 |

(Continued)

OTHER PUBLICATIONS

Yuhao Shan et al., "Remote Detection and Classification of Human Stress Using a Depth Sensing Technique", 2018 First Asian Conference on Affective Computing and Intelligent Interaction (ACII Asia), 2018, IEEE, https://www.researchgate.net/publication/327853040_Remote_Detection_and_Classification_of_Human_Stress_Using_a_Depth_Sensing_Technique/link/5c126fad92851c39ebeb2119/download.
(Continued)

*Primary Examiner* — Rex R Holmes
*Assistant Examiner* — Sana Sahand
(74) *Attorney, Agent, or Firm* — Finnegan, Henderson, Farabow, Garrett & Dunner, LLP

(57) ABSTRACT

Recognizing mental states from physiological signal is a concern not only for medical diagnostics, but also for cognitive science, behavioral studies as well as brain machine interfaces. Embodiments of the present disclosure utilize respiration signals to decipher mental states wherein non-linear baseline drifts in signal is implemented to extract the respiratory features in most effective way. Presence of class imbalance, is effectively rectified using Synthetic Minority Oversampling Technique (SMOTE) to resolve class imbalance problem, which not only increased the classification accuracy, but also reduced classifier bias
(Continued)

towards the majority class, which in turn exceedingly enhanced the classifier sensitivity.

4 Claims, 12 Drawing Sheets

(51) Int. Cl.
    *G16H 50/30*     (2018.01)
    *A61B 5/08*     (2006.01)

(52) U.S. Cl.
    CPC ............ *A61B 5/7267* (2013.01); *A61B 5/746* (2013.01); *G16H 50/30* (2018.01)

(56) References Cited

FOREIGN PATENT DOCUMENTS

| | | |
|---|---|---|
| FR | 3047654 A1 | 8/2017 |
| KR | 101004036 B1 | 12/2010 |

OTHER PUBLICATIONS

Youngjun Cho et al., "DeepBreath: Deep Learning of Breathing Patterns for Automatic Stress Recognition using Low-Cost Thermal Imaging in Unconstrained Settings", DeepBreath_ACII2017, 2017, Research Gate, https://www.researchgate.net/publication/319210001_DeepBreath_Deep_Learning_of_Breathing_Patterns_for_Automatic_Stress_Recognition_using_Low-_Cost_Thermal_Imaging_in_Unconstrained_Settings/link/59d569cb458515140ee44604/download.

\* cited by examiner

STRESS LEVEL MONITORING OF USERS USING A RESPIRATORY SIGNAL AND ALERTING THEREOF

PRIORITY CLAIM

This U.S. patent application claims priority under 35 U.S.C. § 119 to: India Application No. 201921029445, filed on Jul. 22, 2019. The entire contents of the aforementioned application are incorporated herein by reference.

TECHNICAL FIELD

The disclosure herein generally relates to stress level monitoring techniques, and, more particularly, to stress level monitoring of users using a respiratory signal and alerting thereof.

BACKGROUND

Recognizing mental states from physiological signal is a concern not only for medical diagnostics, but also for cognitive science, behavioral studies as well as brain machine interfaces. Prolonged frustration in any individual can cause stress and anxiety, thereby causing damage to his/her mental and physical well-being. Deciphering mental states from physiological signals is one of the requisites for wide range of application spheres including cognitive science, behavioral studies, neuroscience, brain machine interfaces (BMIs) to name a few. In literature, mental state recognition can refer to emotional states, stress, anxiety and/or motor intentions (in case of BMIs). Since, prolonged exposure to stress, anxiety or frustration can lead to serious health issues, it is one of the major concerns in the related fields.

SUMMARY

Embodiments of the present disclosure present technological improvements as solutions to one or more of the above-mentioned technical problems recognized by the inventors in conventional systems. For instance, in one aspect, there is provided a method for stress level monitoring and alerting users thereof. The method comprises obtaining a respiratory signal corresponding to one or more users, wherein the respiratory signal is obtained using one or more sensors at a first time interval within a controlled environment; sequentially performing a mean subtraction technique, a low pass filtering technique, and a baseline drift detection and removal technique on the respiratory signal to obtain a pre-processed respiratory signal for each of the one or more users, wherein the baseline drift detection and removal technique is applied on an output obtained upon applying the low filtering technique to filter baseline drift by (i) identifying one or more troughs in the output, wherein a spline is fitted through the identified one or more troughs and (ii) correcting time series data above the spline; applying a window approach technique on time series data of the pre-processed respiratory signal to extract one or more morphological and one or more statistical features, wherein the one or more statistical features are extracted from a higher order dynamics of the pre-processed respiratory signal for each of the one or more users; ranking, using a feature selection technique, the one or more extracted morphological and the one or more statistical features to obtain a set of unique combinational features for each of the one or more users; and classifying mental state of the one or more users as one of a normal state or an abnormal state by applying one or more classifiers on a set of synthetically balanced features obtained based on the set of unique combinational features. In an embodiment, the step of classifying mental state of the one or more users as one of a normal state or an abnormal state by applying one or more classifiers on the set of synthetically balanced features comprises: adjusting the set of unique combinational features using Synthetic Minority Oversampling Technique (SMOTE) to obtain the set of synthetically balanced features; and applying one or more classifiers on the set of synthetically balanced features to classify mental state of the one or more users as one of a normal state or an abnormal state.

In one embodiment, the feature selection technique comprises a ReliefF algorithm.

In an embodiment, the method may further comprise training a model for each of the one or more users based on the classification of the mental state of one or more users as one of the normal state or the abnormal state.

In an embodiment, the method may further comprise: upon obtaining the trained model, obtaining a respiratory signal corresponding to the one or more users, wherein the respiratory signal is obtained at one or more time intervals for a pre-determined time period; generating, using the trained model, a stress score for each of the one or more users, wherein the stress score is generated for the pre-determined time period.

In an embodiment, the method may further comprise: performing a first comparison of (i) the stress score specific to a first time duration of the pre-determined time period with (ii) a pre-determined threshold, and alerting the one or more users associated thereof based on the first comparison.

In an embodiment, the method may further comprise: performing a second comparison of (i) the stress score specific to the first time duration with (ii) the stress score of a second time duration of the pre-determined time period and alerting the one or more users associated thereof based on the second comparison.

In another aspect, there is provided a system for stress level monitoring and alerting users thereof. The system comprises a memory storing instructions; one or more communication interfaces; and one or more hardware processors coupled to the memory via the one or more communication interfaces, wherein the one or more hardware processors are configured by the instructions to: obtain a respiratory signal corresponding to one or more users, wherein the respiratory signal is obtained using one or more sensors at a first time interval within a controlled environment; sequentially perform a mean subtraction technique, a low pass filtering technique, and a baseline drift detection and removal technique on the respiratory signal to obtain a pre-processed respiratory signal for each of the one or more users, wherein the baseline drift detection and removal technique is applied on an output obtained upon applying the low filtering technique to filter baseline drift by (i) identifying one or more troughs in the output, wherein a spline is fitted through the identified one or more troughs and (ii) correcting time series data above the spline; apply a window approach technique on time series data of the pre-processed respiratory signal to extract one or more morphological and one or more statistical features, wherein the one or more statistical features are extracted from a higher order dynamics of the pre-processed respiratory signal for each of the one or more users; rank, using a feature selection technique, the one or more extracted morphological and the one or more statistical features to obtain a set of unique combinational features for each of the one or more users; and classify mental state of the one or more users as one of a normal state or an abnormal state by applying one or more classifiers on a set of synthetically balanced features obtained based on the set of unique combinational features. In an embodiment, the mental state of the one or more users is classified as one of a normal state or an abnormal state by applying one or more classifiers on the set of synthetically balanced features by: adjusting the set of unique combinational features using Synthetic Minority Oversampling Technique (SMOTE) to obtain a set of synthetically balanced features; and applying one or more classifiers on the set of synthetically balanced features to classify mental state of the one or more users as one of a normal state or an abnormal state.

In one embodiment, the feature selection technique comprises a ReliefF algorithm.

In an embodiment, the one or more hardware processors are further configured by the instructions to train a model for each of the one or more users based on the classification of the mental state of one or more users as one of the normal state or the abnormal state.

In an embodiment, the one or more hardware processors are further configured by the instructions to: obtain a respiratory signal corresponding to the one or more users, wherein the respiratory signal is obtained at one or more time intervals for a pre-determined time period; and generate, using the trained model, a stress score for each of the one or more users, wherein the stress score is generated for the pre-determined time period.

In an embodiment, the one or more hardware processors are further configured by the instructions to: perform a first comparison of (i) the stress score specific to a first time duration of the first pre-determined time period with (ii) a pre-determined threshold, and alerting the one or more users associated thereof based on the first comparison.

In an embodiment, the one or more hardware processors are further configured by the instructions to: perform a second comparison of (i) the stress score specific to the first time duration with (ii) the stress score of a second time duration of the pre-determined time period and alerting the one or more users associated thereof based on the second comparison.

In yet another aspect, there are provided one or more non-transitory machine readable information storage mediums comprising one or more instructions which when executed by one or more hardware processors cause stress level monitoring and alerting users thereof by obtaining a respiratory signal corresponding to one or more users, wherein the respiratory signal is obtained using one or more sensors at a first time interval within a controlled environment; sequentially performing a mean subtraction technique, a low pass filtering technique, and a baseline drift detection and removal technique on the respiratory signal to obtain a pre-processed respiratory signal for each of the one or more users, wherein the baseline drift detection and removal technique is applied on an output obtained upon applying the low filtering technique to filter baseline drift by (i) identifying one or more troughs in the output, wherein a spline is fitted through the identified one or more troughs and (ii) correcting time series data above the spline; applying a window approach technique on time series data of the pre-processed respiratory signal to extract one or more morphological and one or more statistical features, wherein the one or more statistical features are extracted from a higher order dynamics of the pre-processed respiratory signal for each of the one or more users; ranking, using a feature selection technique, the one or more extracted morphological and the one or more statistical features to obtain a set of unique combinational features for each of the one or more users; and classifying mental state of the one or more users as one of a normal state or an abnormal state by applying one or more classifiers on a set of synthetically balanced features obtained based on the set of unique combinational features. In an embodiment, the step of classifying mental state of the one or more users as one of a normal state or an abnormal state by applying one or more classifiers on the set of synthetically balanced features comprises: adjusting the set of unique combinational features using Synthetic Minority Oversampling Technique (SMOTE) to obtain the set of synthetically balanced features; and applying one or more classifiers on the set of synthetically balanced features to classify mental state of the one or more users as one of a normal state or an abnormal state.

In one embodiment, the feature selection technique comprises a ReliefF algorithm.

In an embodiment, the instructions which when executed by the one or more hardware processors may further cause training a model for each of the one or more users based on the classification of the mental state of one or more users as one of the normal state or the abnormal state.

In an embodiment, the instructions which when executed by the one or more hardware processors may further cause: upon obtaining the trained model, obtaining a respiratory signal corresponding to the one or more users, wherein the respiratory signal is obtained at one or more time intervals for a pre-determined time period; and generating, using the trained model, a stress score for each of the one or more users, wherein the stress score is generated for the pre-determined time period.

In an embodiment, the instructions which when executed by the one or more hardware processors may further cause: performing a first comparison of (i) the stress score specific to a first time duration of the pre-determined time period with (ii) a pre-determined threshold, and alerting the one or more users associated thereof based on the first comparison.

In an embodiment, the instructions which when executed by the one or more hardware processors may further cause: performing a second comparison of (i) the stress score specific to the first time duration with (ii) the stress score of a second time duration of the pre-determined time period and alerting the one or more users associated thereof based on the second comparison.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
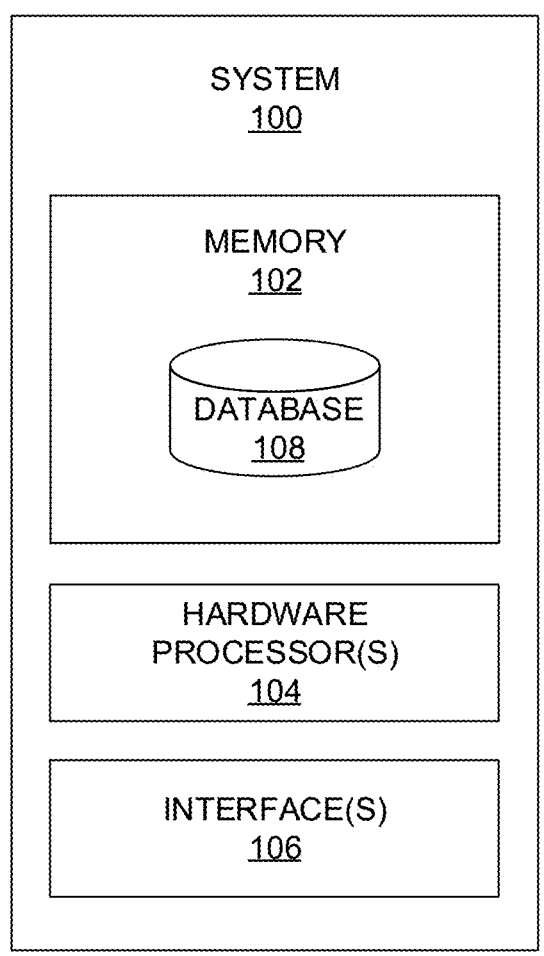
FIG. 1 depicts illustrates an exemplary block diagram of a system for monitoring mental state of users and alerting thereof, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims. Deciphering mental states from physiological signals is one of the requisites for wide range of application spheres including cognitive science, behavioral studies, neuroscience, brain machine interfaces (BM's) to name a few. In literature, mental state recognition can refer to emotional states, stress, anxiety and/or motor intentions (in case of BM's). Since, prolonged exposure to stress, anxiety or frustration can lead to serious health issues, it is one of the major concerns of research in the related fields. Researchers have designed an experimental setup which provided users with stimuli evoking frustration response. Physiological signals such as GSR (Galvanic Skin Response), BVP (Blood Volume Pulse) were collected and studied to classify users based on their mental state. Furthermore, stress generated in drivers were studied using data collected through various sensors such as ECG (Electrcardiogram), EMG (Electromyogram), GSR and respiration signal extracted from chest activity expansion. Other works have also shown that its possible to detect stress in subjects based on subjects' physiological signals such as GSR, BVP, Pupil diameter, skin temperature, EEG and other signals as mentioned above, using all of them together or few of them at a time.

It has been conventionally studied that parameters of physiological signal vary considerably with changing cognitive load on the subject. Literature suggests that the information about the mental state of the subject can be identified through the features extracted from various physiological signals such as Electroencephalogram (EEG), Photoplethysmogram (PPG), Galvanic Skin Response (GSR), Electrooculogram (EOG), Electromyogram (EMG), temperature, respiration to name a few. Likewise, prediction of emotional state from physiological signals have been studied for stress and anxiety detection. In the art, it was shown that respiratory signal reflects cognitive activities. Researchers have monitored breathing waveform in order to study how they are affected by mental load. Most of these above mentioned works rely on more than one type of physiological signals, whereas none have attempted to detect frustration from only respiratory signals.

In present disclosure, primary motivation is to solely use the respiratory signals in deciphering subjects' mental states of normal and frustration. The respiratory signal is one of the most common physiological signal that can be easily acquired with minimum obtrusion compared to EEG, EOG and/or GSR. Moreover, research also indicates that breath signals can be reproduced from PPG signals itself. A new approach of nonlinear baseline drift detection and removal is incorporated by the present disclosure, in an attempt to extract relevant respiratory features efficiently. One of the major challenge of bio-signals collated through affective studies is a presence of class imbalance. Such imbalance demands minor class oversampling or major class undersampling techniques are generally incorporated, which has its own issues. Here, the problem of class imbalance is handled efficiently by employing SMOTE algorithm. Feature selection based on feature ranking is obtained by using the ReliefF algorithm. A performance analysis of the extracted features before and after handling class imbalance is presented by classifying with various classifiers viz. Support Vector Machine (SVM), K-Nearest Neighbour (KNN), Naive Bayesian (NB), Multi-Layer Perceptron (MLP), Random Forest (RF) and Trees J48.

Embodiments of the present disclosure implements mental state monitoring (e.g., frustration/stress detection) from respiration signals alone. Use respiration signal as described by the present disclosure has few advantages, namely:

1) Respiration/breath signals can be unobstrusively acquired using different sensors, viz, respiration belt, pneumotachograph, accelerometer to name a few, which makes collection of the signal quite easy.

2) Breathing pattern can be re-generated from PPG signal as shown in conventional research.

Researchers (e.g., Choubeila et al.) have showed stress detection is possible using only PPG signal. However, breathing signal is not analyzed and feature extraction has been performed on the PPG signal itself.

Referring now to the drawings, and more particularly to FIGS. 1 through 8, where similar reference characters denote corresponding features consistently throughout the figures, there are shown preferred embodiments and these embodiments are described in the context of the following exemplary system and/or method.

FIG. 1 depicts illustrates an exemplary block diagram of a mental state monitoring system for monitoring mental state of users and alerting thereof, in accordance with an embodiment of the present disclosure. The system 100 may also be referred as 'monitoring system' or 'mental state monitoring and alerting system' and may be interchangeably used hereinafter. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information, for example, time series data of respiratory signals of various users, pre-processed respiratory signals of users, features extracted (e.g., morphological features, statistical features, synthetically balanced features which indicate balance between normal state and abnormal state of users, and the like. In an embodiment, the memory 102 may store (or stores) one of more techniques (e.g., mean subtraction technique, low pass filtering technique, baseline drift detection and removal technique, feature selection technique, classifiers, and the like). The memory 102 further comprises (or may further comprise) information pertaining to input(s)/output(s) of each step performed by the systems and methods of the present disclosure. More specifically, information pertaining to time series data of respiratory signal obtained from various users (e.g., captured via sensors that are either attached to the users or are in close proximity of users), pre-processing methods, and the like, may be stored in the memory 102. In other words, input(s) fed at each step and output(s) generated at each step are comprised in the memory 102, and can be utilized in further processing and analysis.

Figure 2:
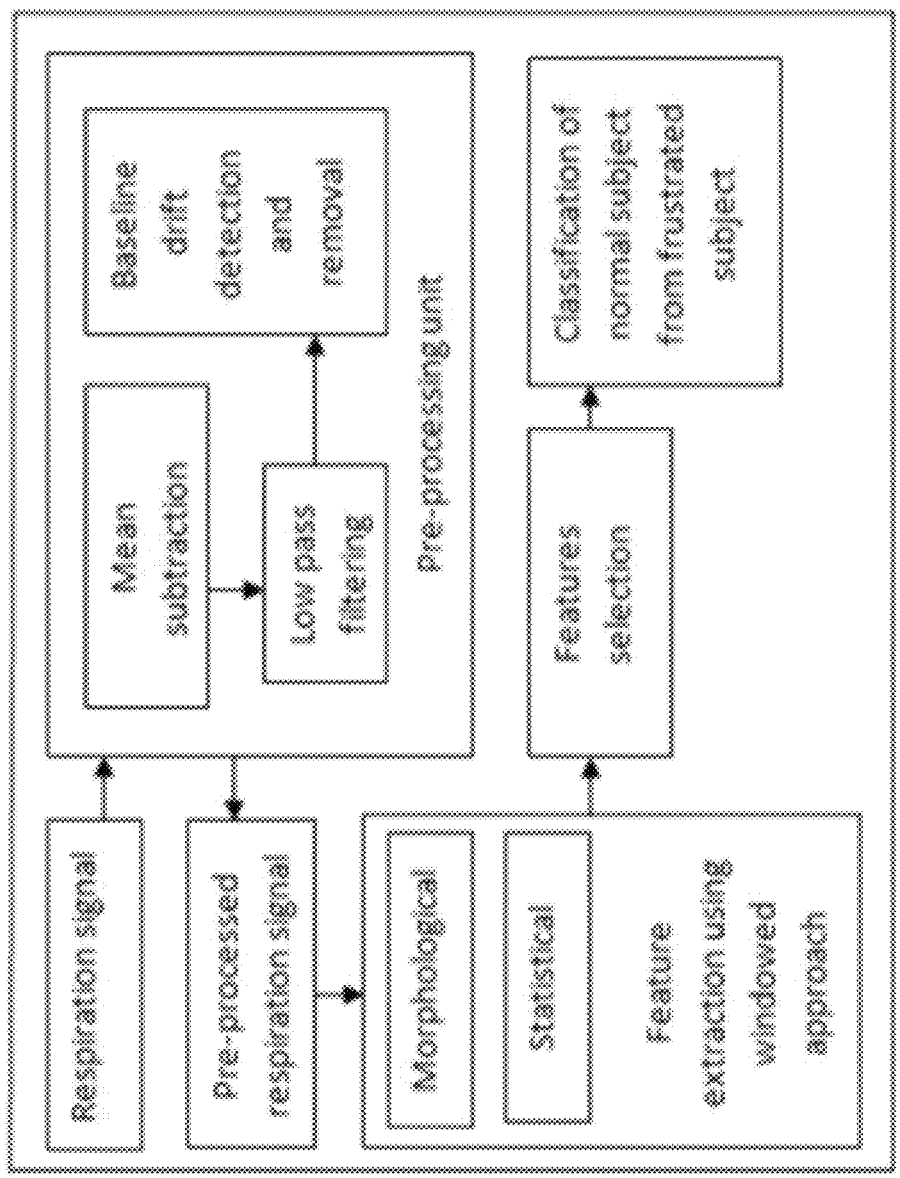
FIG. 2 depicts an exemplary block diagram of the mental state monitoring and alerting system of FIG. 1 in accordance with an embodiment of the present disclosure.

FIG. 2, with reference to FIG. 1, depicts an exemplary block diagram of the mental state monitoring and alerting system 100 in accordance with an embodiment of the present disclosure.

Figure 3:
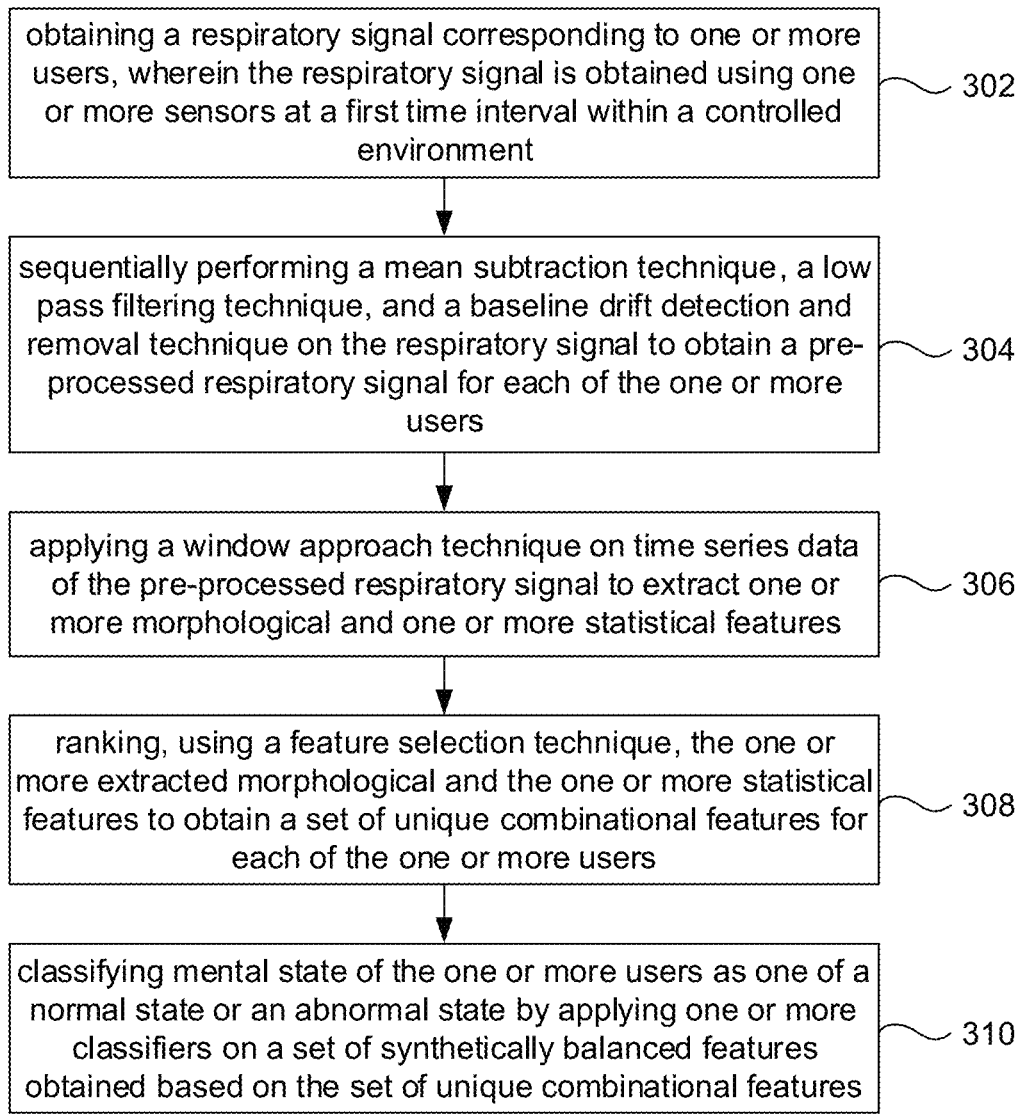
FIG. 3 is an exemplary flow diagram illustrating a method for mental state monitoring and alerting users thereof using the system of FIG. 1-2, in accordance with an embodiment of the present disclosure.
Figure 4A:
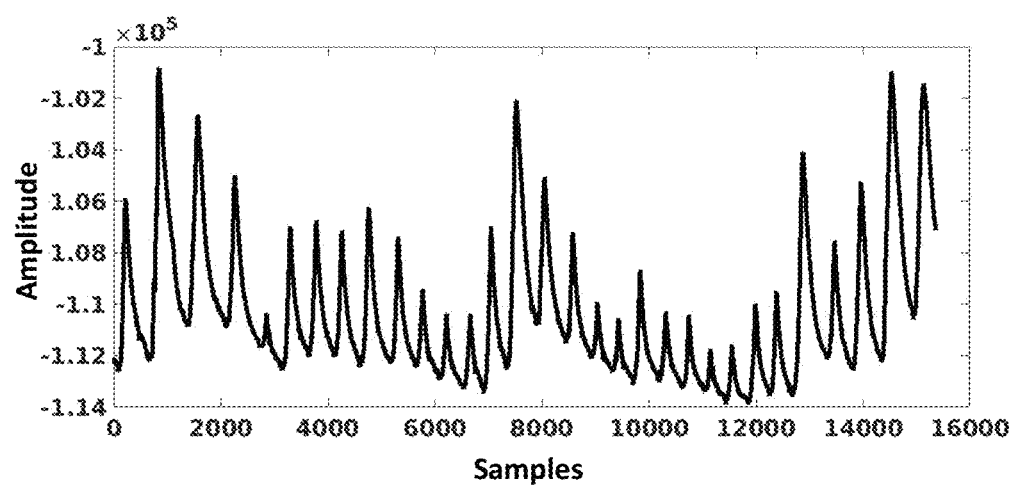
FIGS. 4A-4E depict various pre-processing techniques being applied on respiratory signal of users to obtain a pre-processed respiratory signal, in accordance with an embodiment of the present disclosure.
Figure 4B:
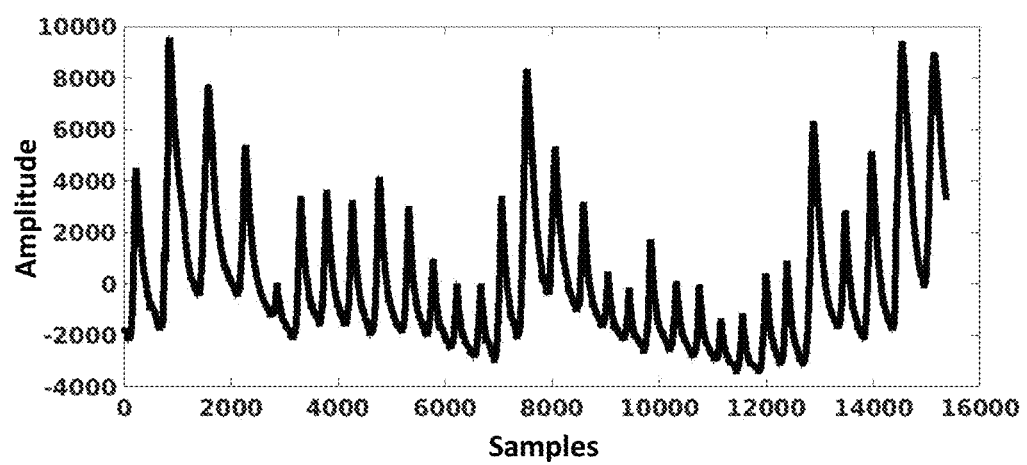
Figure 4C:
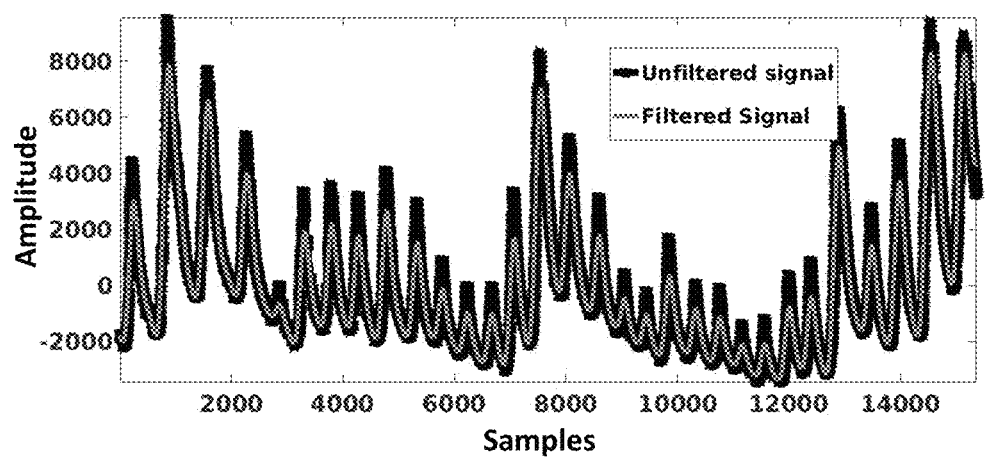
Figure 4D:
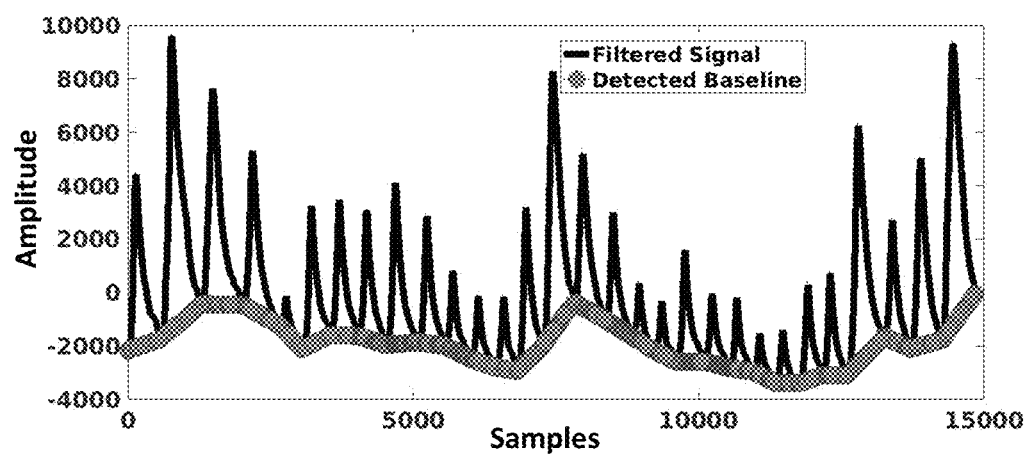
Figure 4E:
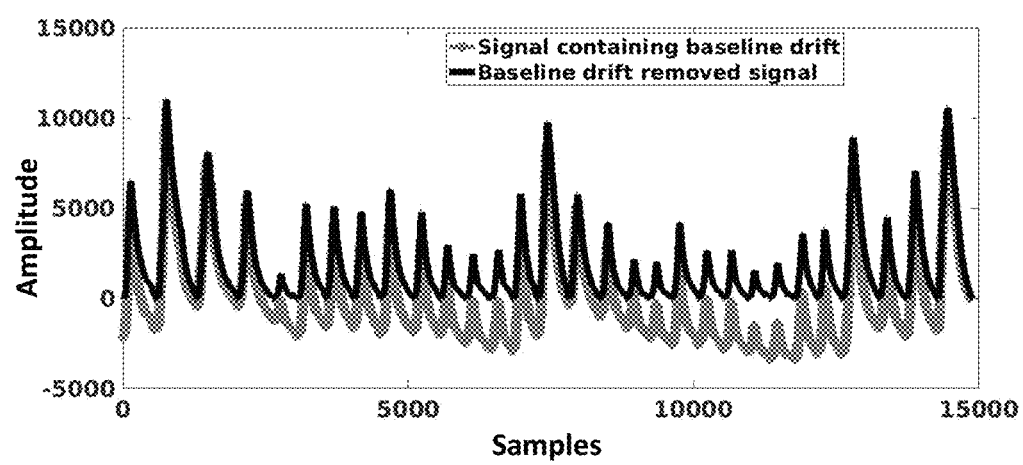
Figure 5:
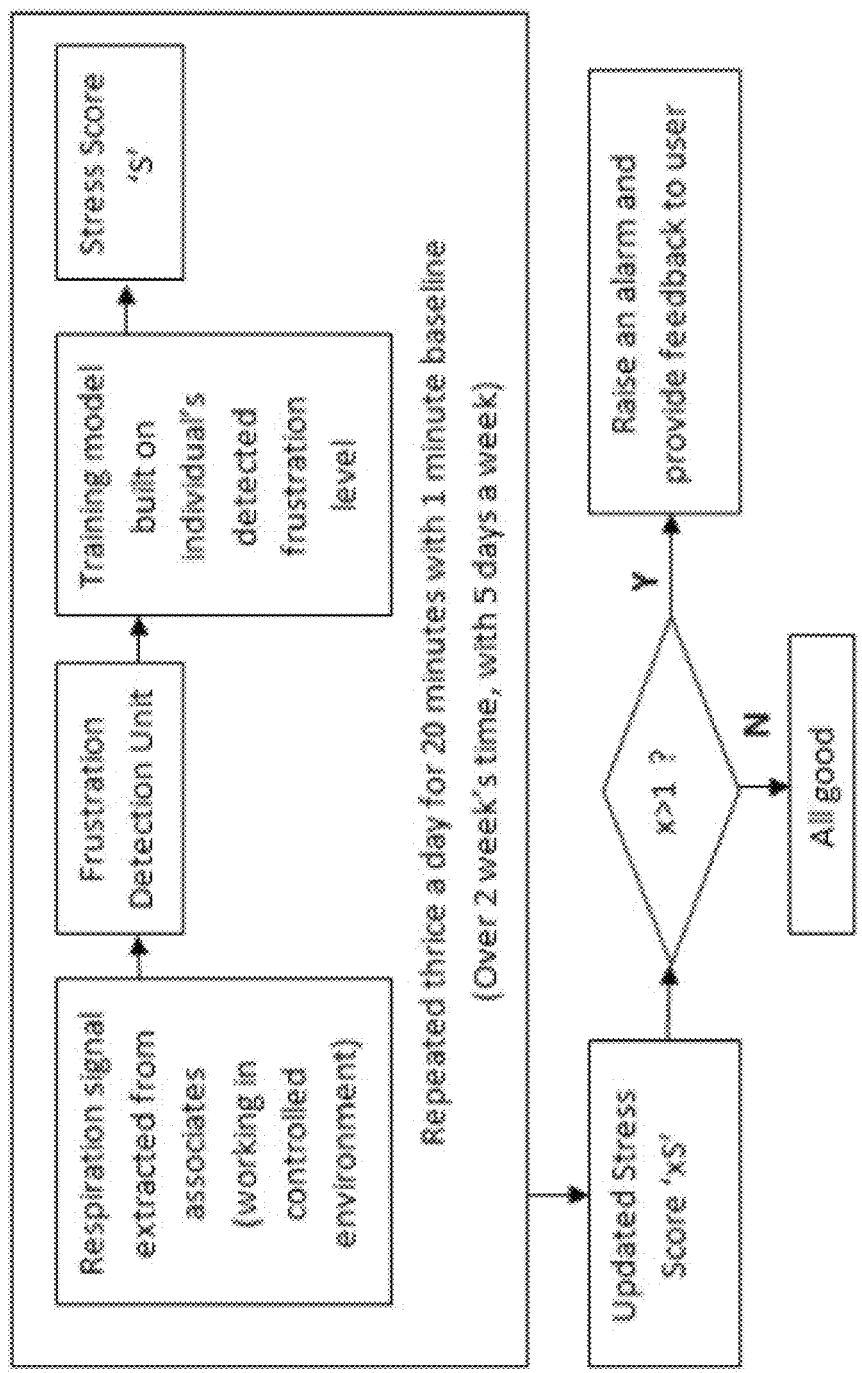
FIG. 5 depicts an example block diagram illustrating training of a model and generation of stress score for each user, in accordance with an embodiment of the present disclosure.

FIG. 3, with reference to FIGS. 1-2, is an exemplary flow diagram illustrating a method for mental state monitoring and alerting users thereof using the system 100 of FIG. 1-2, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1-2, graphical representations as depicted in FIGS. 4A through 4E, a flow chart as depicted in FIG. 5, and the flow diagram as depicted in FIG. 3. At step 302 of the present disclosure, the one or more hardware processors 104 obtain a respiratory signal corresponding to one or more users (e.g., refer FIG. 4A), wherein the respiratory signal is obtained using one or more sensors at a first time interval within a controlled environment. Let's say, every user (e.g., associate/employee) in an office was asked to provide physiological data (PPG/respiration signal) through the system 100. At step 304 of the present disclosure, the one or more hardware processors 104 sequentially perform a mean subtraction technique, a low pass filtering technique, and a baseline drift detection and removal technique on the respiratory signal to obtain a pre-processed respiratory signal for each of the one or more users. For instance, pre-processing of the physiological signals is essential for correctly analyzing and extracting the relevant features. FIGS. 4A-4E depict various pre-processing techniques being applied on respiratory signal of users to obtain a pre-processed respiratory signal, in accordance with an embodiment of the present disclosure. For instance, FIG. 4A depicts raw breath (respiratory) signal in accordance with an embodiment of the present disclosure. Initially the respiratory signal is mean subtracted as depicted in FIG. 4B (e.g., FIG. 4B depicting mean corrected signal), followed by filtering (by applying a low pass filtering technique. High frequency noise components are present in this signal, which requires low pass filtering. A section of this filtered signal along with its unfiltered form is shown in FIG. 4C. A Butterworth 2nd order low pass filter with a cut off frequency of 10 Hz was used by the present disclosure to get rid of the higher frequency noise components. It can be seen that the baseline of this filtered signal keeps varying with time. Furthermore, a baseline drift is present in the filtered signal, which needs to get corrected or else features values computed would turn out to be inaccurate. As can be seen from FIGS. 4B and 4C, the signal processing steps of mean subtraction, linear detrending, nonlinear detrending did not help to get rid of the nonlinear baseline rift. Therefore, the present disclosure employs the baseline drift detection and removal technique that is applied on an output obtained upon applying the low filtering technique to filter baseline drift by (i) identifying one or more troughs in the output, wherein a spline is fitted through the identified one or more troughs and (ii) correcting time series data above the spline. In other words, baseline drift correction is implemented by the system 100, in which all troughs in the entire filtered signal are detected. A spline is further fitted through them, and the data part above the nonlinear spline is corrected down to zero on the Y axis. FIG. 4D with reference to FIGS. 1 through 4C, depicts detected (or identified) troughs of the baseline in accordance with an embodiment of the present disclosure. FIG. 4E, with reference to FIGS. 1 through 4D, depicts filtered signal with baseline drift and the baseline drift corrected signal.

At step 306 of the present disclosure, the one or more hardware processors 104 apply a window approach technique on time series data of the pre-processed respiratory signal to extract one or more morphological and one or more statistical features. In the present disclosure, the one or more statistical features have been extracted from a higher order dynamics (e.g., a first order dynamics/derivative and/or a second order dynamics/derivative with respect to time) of the pre-processed respiratory signal for each of the one or more users. Once, the signal is cleaned, heuristically different morphological and statistical features are extracted as given below:

1) Statistical Features—Let the respiratory signal be x(t). The features that have been considered are: Mean, median, inter-quartile range, standard deviation, kurtosis, skewness of x(t), dx(t)/dt and $d^2x(t)/dt^2$ 2) Morphological Features—Inspiratory cycle, Expiratory cycle, Breaths per minute, Tidal volume, Expiratory ratio, Inspiratory ratio, Max inspiratory flow, Minimum expiratory flow, Inspiratory ratio, Expiratory ratio, Breath ratio, Inspiratory volume, Expiratory volume, Stretch, Minute volume, etc.

The above mentioned features are computed and extracted from the data using a windowed approach. Over three different windows, i.e., 15 sec window, 30 sec window and 15 sec window with 50% overlap, latter one turned out to be the most effective one in terms of classification result. A combination of these statistical and morphological features are used as input to the classifier in order to classify the stress level of an individual as whether he is normal or frustrated. The five most relevant morphological features which produces the best classification results for this 2 class problem (normal=class1, frustrated=class2) are:

1) Inspiratory Cycle=Ti where Ti is the time taken to reach from a trough to the next immediate peak
2) Expiratory Cycle=Te where Te is the time taken to reach from a peak to the next immediate trough
3) Expiratory ratio=Te/Ti+Te
4) Inspiratory volume which is the area under peak for the duration of Ti
5) Stretch which is the difference between the peak and trough of a respiratory cycle.

At step 308, the one or more hardware processors 104 rank, using a feature selection technique (e.g., ReliefF algorithm, and the like.), the one or more extracted morphological and the one or more statistical features to obtain a set of unique combinational features for each of the one or more users. At step 310, the one or more hardware processors 104 classify mental state of the one or more users as one of a normal state or an abnormal state by applying one or more classifiers on a set of synthetically balanced features obtained based on the set of unique combinational features. In the present disclosure, mental state of the one or more users is classified as one of a normal state or an abnormal state by applying one or more classifiers on the set of synthetically balanced features obtained based on the set of unique combinational features by: adjusting the set of unique combinational features using Synthetic Minority Oversampling Technique (SMOTE) to obtain the set of synthetically balanced features; and applying one or more classifiers on the set of synthetically balanced features to classify mental state of the one or more users as one of a normal state or an abnormal state. In other words, the set of synthetically balanced features are obtained by adjusting the set of unique combinational features using Synthetic Minority Oversampling Technique (SMOTE).

Commonly used approaches such as oversampling of minority class, or under sampling of majority class, synthetic data generation or cost effective learning are used to adjust the class distribution of such data set. SMOTE (Synthetic Minority Over-Sampling Technique) as known in the art technique suggests a combination of over-sampling the minority (abnormal) class and under-sampling the majority (normal) class which is proved to achieve better classifier performance than only under-sampling the majority class or only over-sampling the minority class. It effectively forces the decision region of the minority class to become more general. The problem with randomly under-sampling or oversampling is that, it no doubt balances the data sets but also sometimes lead to loss or distortion of useful information. It should be noted that SMOTE cannot be directly applied on the entire data set. Then there lies a high probability of same data getting repeated. In order to get rid of this, first the data is split into test and train set, and then SMOTE is applied over the training data set for proper validation of the testing set.

This kind of monitoring system can also be used to provide continuous feedback to employees about their mental health and also in turn help them to control their stress levels.

Further, a model was trained by the system 100. The model was built/trained for each of the one or more users based on the classification of the mental state of one or more users as one of the normal state or the abnormal state. Upon obtaining the trained model, a respiratory signal corresponding to the one or more users was obtained at one or more time intervals for a pre-determined time period, and a stress score was generated for each of the one or more users, wherein the stress score is generated for the pre-determined time period. FIG. 5, with reference to FIGS. 1 through 4E, depicts an example block diagram illustrating training of a model and generation of stress score for each user, in accordance with an embodiment of the present disclosure. In other words, on a daily basis for a certain duration of office hours (let's say thrice in a day for 20 minutes over 5 days a week), when employees are at their workstation, these physiological/respiratory signals were collated for each of them. Throughout this 20 minutes of data collection, for initial 1 minute the subject was asked to relax, and the corresponding baseline data was collected. For the next 19 minutes, his/her actual data corresponding to the work he/she is doing was recorded. This would constitute to be quite a good amount of data which could be studied in order to track his/her mental fatigue, stress level, frustration etc. over a period of 1 month. This new test data was fed to the training model in order to get the new updated stress/frustration level. For instance, a first comparison of (i) the stress score specific to a first time duration (e.g., first and second week) of the pre-determined time period (e.g., say 30 days) with (ii) a pre-determined threshold (e.g., say 1) was performed, and the one or more users associated thereof were alerted based on the first comparison. Another comparison (e.g., a second comparison) of (i) the stress score specific to the first time duration (e.g., first and second week) with (ii) the stress score of a second time duration (e.g., third and fourth week) of the pre-determined time period (e.g., the same 30 days) was performed, and the one or more users associated thereof were alerted based on the second comparison.

The above description can be better understood by way of following non-construing example:

Over a period of say 30 days, each individual would have a 'Stress Score' corresponding to each day at work. This can be tracked by the management on a weekly basis as below:

Assuming initially from the training model an individual had a stress score of S. After first 2 weeks of data collection, suppose the consolidated score is xS:

1) where $x \geq 1$
System Response: Raise an alarm and provide this feedback to the user.
2) For $x<1$
System Response: Mention to user that all is good.
After another 2 weeks (3rd and 4th week) of data collection, any of the following situations may arise:

a) Associate having condition 1) goes to 2)
System Response: Mention to user that situation has improved and no action required.
  b) Associate having condition 2) goes to 1)
System Response: Raise an alarm and provide this feedback to the user.
  c) Associate having condition 2) remains at 2)
System Response: Mention to user that all is good.
  d) Associate having condition 1) remains at 1)
System Response: Advice the participant to change his/her work schedules, engage in mental exercises, or try changing physical activities, diet, etc.

Figure 6:
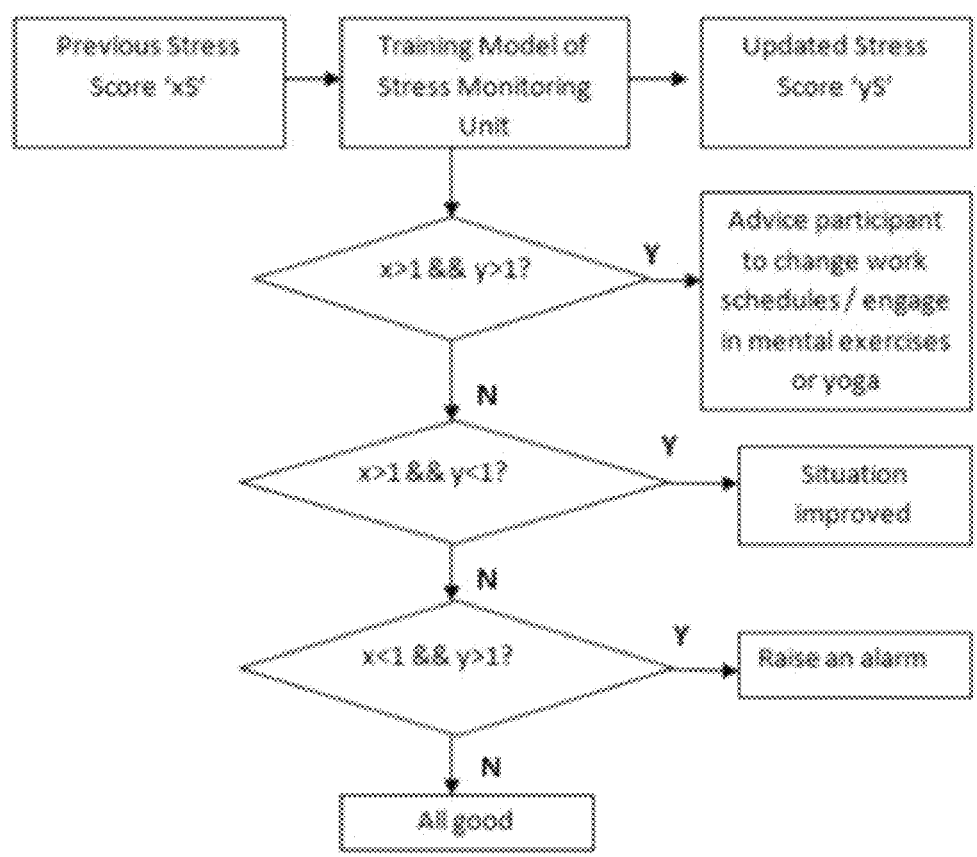
FIG. 6 illustrates stress level monitoring and altering users thereof, in accordance with an embodiment of the present disclosure.

The above example has been depicted in FIG. 6 which illustrates stress level monitoring and altering users thereof in accordance with an embodiment of the present disclosure.

Figure 7:
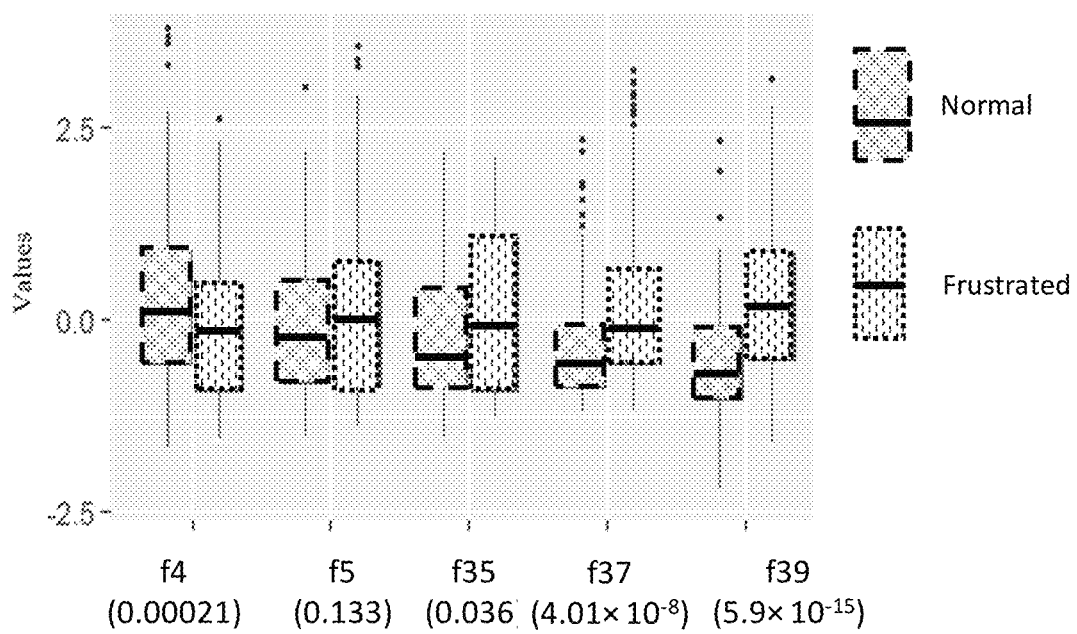
FIG. 7 depicts a box plot of ANOVA of the top five most relevant features mentioned above, in accordance with embodiment of the present disclosure.
Figure 8:
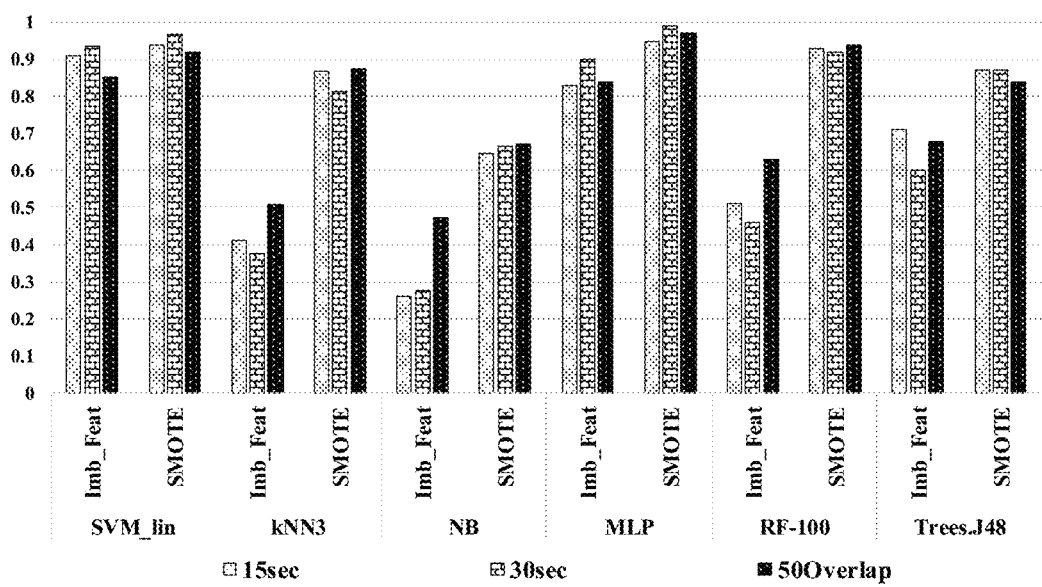
FIG. 8, with reference to FIGS. 1 through 7, depicts a graphical representation that illustrates True negative rate (TNR) enhancement by implementing SMOTE to cope with data imbalance, in accordance with an embodiment of the present disclosure.

Systems and methods of the present disclosure were tested on the publicly available Affective Pacman data set as known in the art, where the present disclosure successfully classified normal subjects from frustrated subjects. FIG. 7, depicts a box plot of ANOVA of the top five most relevant features mentioned above, in accordance with embodiment of the present disclosure. The plots show a visible segregation between the normal and frustrated mental states. This result further motivated the present disclosure to apply classification algorithms on the extracted feature set. In this particular dataset, number of frustrated trials were much lesser compared to normal trials. This class imbalance was handled using Synthetic Minority Oversampling Technique (SMOTE). FIG. 8, with reference to FIGS. 1 through 7, depicts a graphical representation that illustrates True negative rate (TNR) enhancement by implementing SMOTE to cope with data imbalance, in accordance with an embodiment of the present disclosure. In other words, TNR (True Negative Rate) enhances exceedingly for SMOTE generated features compared to its imbalanced counterpart (Imb Feat). Below Table I represents Classification Accuracy (CA) and True positive rate (TPR) for the various classifiers as mentioned above, for the several windows, for both original imbalanced feature set (Imb Feat) and the SMOTE generated feature set (SMOTE). These are the averaged results of 10-fold cross validation, over all the subjects. For every classifier, every window configuration, CAs are always better with SMOTE generated features, while the TPR values are comparable for both Imb Feat and SMOTE feature sets. The MLP classifier for 30 sec window is seen to perform best, with CA, TPR and TNR of 97.9%, 92.6% and 99.3%.

TABLE 1

Classification accuracy (CA) and True positive rate (TPR) comparing the efficacy of SMOTE generated feature set to compensate imbalanced respiratory feature set.

| | | CA | | | TPR | | |
|---|---|---|---|---|---|---|---|
| | | Win15 | Win30 | Win15Ovlp50 | Win15 | Win30 | Win15Ovlp50 |
| SVM_lin | Imb_Feat* | 0.891 | 0.952 | 0.891 | 0.898 | 0.958 | 0.921 |
| | SMOTE | 0.923 | 0.957 | 0.919 | 0.901 | 0.948 | 0.901 |
| kNN3 | Imb_Feat | 0.682 | 0.719 | 0.749 | 0.823 | 0.887 | 0.867 |
| | SMOTE | 0.753 | 0.727 | 0.773 | 0.859 | 0.847 | 0.859 |
| NB | Imb_Feat | 0.627 | 0.512 | 0.632 | 0.801 | 0.642 | 0.703 |
| | SMOTE | 0.631 | 0.568 | 0.637 | 0.818 | 0.632 | 0.712 |
| MLP | Imb_Feat | 0.890 | 0.933 | 0.898 | 0.925 | 0.951 | 0.932 |
| | SMOTE | 0.931 | 0.979 | 0.949 | 0.926 | 0.953 | 0.931 |
| RF-100 | Imb_Feat | 0.812 | 0.790 | 0.845 | 0.961 | 0.967 | 0.951 |
| | SMOTE | 0.924 | 0.911 | 0.930 | 0.920 | 0.975 | 0.945 |
| Trees J4.8 | Imb_Feat | 0.828 | 0.787 | 0.786 | 0.887 | 0.838 | 0.847 |
| | SMOTE | 0.862 | 0.851 | 0.828 | 0.852 | 0.841 | 0.851 |

*CA—Classification Accuracy,
TPR—True Positive Rate,
Imb Feat—Imbalanced feature set,
SVM lin—linear SVM,
kNN3—k Nearest Neighbour, k = 3,
NB—Naive Bayesian,
MLP—Multi Layer Perceptron,
RF-100—Random Forest with 100 trees The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for stress level monitoring of one or more users, comprising:

acquiring unobstrusively, using one of a respiration belt, a pneumotachograph, and an accelerometer, a respiratory signal corresponding to the one or more users, at a first time interval within a controlled environment;

obtaining, by one or more hardware processors via one or more communication interfaces, the respiratory signal corresponding to the one or more users;

sequentially performing, by the one or more hardware processors, a mean subtraction technique, and a low pass filtering technique on the respiratory signal to obtain an output;

performing, by the one or more hardware processors, a baseline drift detection and removal technique on the output to obtain a pre-processed respiratory signal for each of the one or more users, wherein the baseline drift detection and removal technique is applied on the output to filter baseline drift by (i) identifying one or more troughs in the output, wherein a spline is fitted through the identified one or more troughs and (ii) correcting time series data of the output, above the spline, to zero;

applying, by the one or more hardware processors, a window approach technique on the pre-processed respiratory signal to extract one or more morphological and one or more statistical features, wherein the one or more statistical features are extracted from a higher order dynamics of the pre-processed respiratory signal for each of the one or more users, wherein the window approach technique comprises a 15 seconds window, a 30 seconds window and a second 15 second window with 50% overlap, and wherein the one or more morphological features extracted from the pre-processed respiratory signal comprises inspiratory cycle, expiratory cycle, breath per minute, tidal volume, expiratory ratio, inspiratory ratio, max inspiratory flow, minimum expiratory flow, breath ratio, inspiratory volume, expiratory volume, Stretch and Minute volume;

ranking, by the one or more hardware processors, using a feature selection technique, the one or more extracted morphological and the one or more statistical features to obtain a set of unique combinational features of the statistical and morphological features, for each of the one or more users;

adjusting, by the one or more hardware processors, the set of unique combinational features using Synthetic Minority Oversampling Technique (SMOTE) to obtain a set of synthetically balanced features, wherein a dataset of the set of unique combinational features is split into a testing dataset and a training dataset to avoid high probability of same data getting repeated, and then SMOTE is applied over the training dataset for validation of the testing data set and to obtain the set of synthetically balanced features;

classifying, by the one or more hardware processors, a mental state of the one or more users as one of a normal state or an abnormal state by applying one or more classifiers on the set of synthetically balanced features;

training, by the one or more hardware processors, a model for each of the one or more users based on the mental state of the one or more users as one of the normal state or the abnormal state;

upon obtaining the trained model, obtaining, by the one or more hardware processors, the respiratory signal corresponding to the one or more users, wherein the respiratory signal is obtained at one or more time intervals for a pre-determined time period;

generating, by the one or more hardware processors, using the trained model, a stress score for each of the one or more users, wherein the stress score is generated for the pre-determined time period; and raising, by the one or more hardware processors, an alarm in response to the stress score, to alert the one or more users associated thereof, thereby providing continuous feedback to the one or more users about the mental state and in turn help the one or more users to control their stress levels.

2. The processor implemented method as claimed in claim 1, wherein the feature selection technique comprises a ReliefF algorithm.

3. The processor implemented method as claimed in claim 1, further comprising: performing a first comparison of (i) the stress score specific to a first time duration of the pre-determined time period with (ii) a pre-determined threshold, and alerting the one or more users associated thereof based on the first comparison.

4. The processor implemented method as claimed in claim 3, further comprising: performing a second comparison of (i) the stress score specific to the first time duration with (ii) the stress score of a second time duration of the pre-determined time period and alerting the one or more users associated thereof based on the second comparison.

* * * * *